(12) United States Patent
Vacher et al.

(10) Patent No.: US 10,100,276 B2
(45) Date of Patent: Oct. 16, 2018

(54) USE OF A FILTER FOR DEFROSTING CELLS

(71) Applicant: GENBIOTECH, Antibes (FR)

(72) Inventors: Dominique Vacher, Mougins (FR); Jean-Noël Gouze, Vallauris (FR); Yannis Guillemin, Villeneuve-Loubet (FR)

(73) Assignee: GENBIOTECH, Antibes (FR)

( * ) Notice: Subject to any disclaimer, the term of this patent is extended or adjusted under 35 U.S.C. 154(b) by 75 days.

(21) Appl. No.: 14/900,511

(22) PCT Filed: Jun. 27, 2014

(86) PCT No.: PCT/IB2014/062664
§ 371 (c)(1),
(2) Date: Dec. 21, 2015

(87) PCT Pub. No.: WO2014/207716
PCT Pub. Date: Dec. 31, 2014

(65) Prior Publication Data
US 2016/0369231 A1    Dec. 22, 2016

(30) Foreign Application Priority Data

Jun. 27, 2013  (WO) .................. PCT/IB2013/055286

(51) Int. Cl.
*A01N 1/02* (2006.01)
*B01L 3/00* (2006.01)
*C12N 5/00* (2006.01)
*C12N 5/073* (2010.01)

(52) U.S. Cl.
CPC ......... *C12N 5/0603* (2013.01); *A01N 1/0236* (2013.01); *B01L 3/5021* (2013.01); *C12N 5/00* (2013.01); *B01L 2300/042* (2013.01); *B01L 2300/0681* (2013.01); *B01L 2300/165* (2013.01); *C12N 2506/25* (2013.01); *C12N 2527/00* (2013.01)

(58) Field of Classification Search
CPC ............. A61K 2300/00; A61K 38/177; A61K 38/1774; A61K 45/06; A61K 38/168; A61K 38/00; A61K 38/10; A61K 38/16; A61K 38/164; A61K 38/17; A61K 38/1703; A61K 38/1709; A61K 38/1767; A61K 38/38; A61K 38/45; A61K 9/00; A61K 35/51; A61K 35/12; A61K 38/22; A61K 38/48; A61K 47/48246; A61K 47/48338; A61K 47/48361; A61K 9/0048; A61K 38/482; A61K 38/4886; A61K 38/4893; A61K 47/6415; A01N 1/0236; B01L 2300/042; B01L 2300/0681; B01L 2300/165; B01L 3/5021; C12N 2506/25; C12N 2527/00; C12N 5/00; C12N 5/0603
See application file for complete search history.

(56) References Cited

U.S. PATENT DOCUMENTS 5,776,769 A    7/1998  Critser

FOREIGN PATENT DOCUMENTS

| WO | 96/30274 A1 | 10/1996 |
|----|-------------|---------|
| WO | 2005/069766 A2 | 8/2005 |

OTHER PUBLICATIONS

Calmels, B., et al., "Technical Report: Preclinical Evaluation of an Automated Closed Fluid Management Device: Cytomate™, for Washing Out DMSO From Hematopoietic Stem Cell Grafts After Thawing," Bone Marrow Transplantation 31(9):823-828, May 2003.
International Search Report dated Nov. 13, 2014, issued in corresponding International Application No. PCT/IB2014/062664, filed Jun. 7, 2014, 4 pages.
Zhou, X., et al., "A Dilution-Filtration System for Removing Cryoprotective Agents," Journal of Biomechanical Engineering 133(2):021007-1-021007-7, Feb. 2011.

*Primary Examiner* — Deborah K Ware
(74) *Attorney, Agent, or Firm* — Morgan, Lewis & Bockius LLP

(57) ABSTRACT

The invention relates to a method for cell defrosting, comprising a step of defrosting a cell suspension consisting of a freezing medium and of cells, followed by a step of removing said freezing medium by filtration, said step of removing the freezing medium being carried out without the previous or simultaneous supply of medium. In particular, the filter is hydrophobic or, before addition of the cell suspension to be frozen, has been covered with a hydrophobic liquid forming a temporary barrier between the filter and the cell suspension. During defrosting, said hydrophobic liquid is removed by the application of a driving force which makes the liquid pass through the filter.

21 Claims, 3 Drawing Sheets

USE OF A FILTER FOR DEFROSTING CELLS

Figure 1:
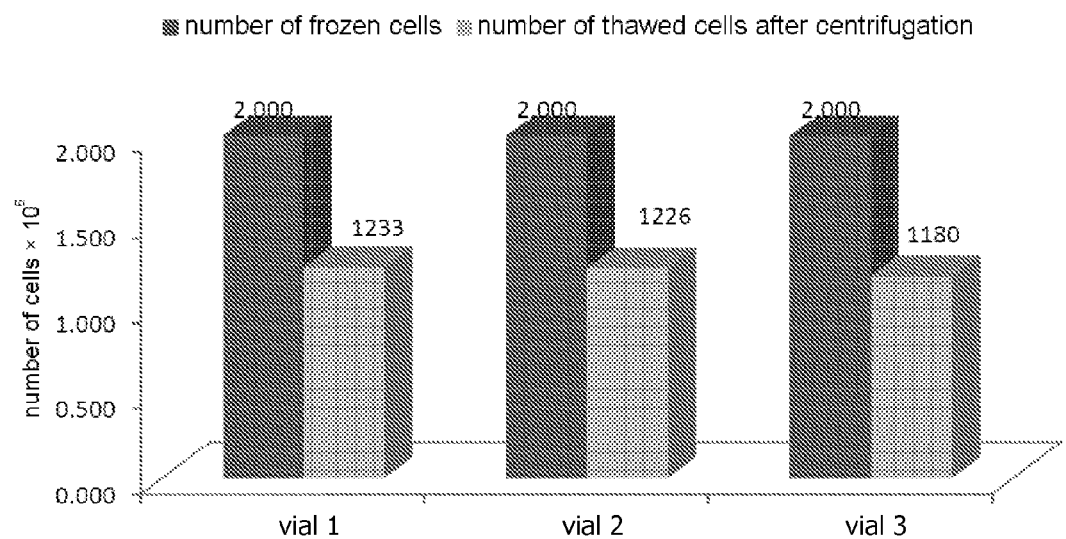

The present invention relates to the field of cell culture. More specifically, it relates to a method for thawing cells which is faster and easier than the conventional methods.

In many situations, the maintenance of cell cultures requires them to be frozen and to be stored at a temperature of less than or equal to −130° C.

During freezing, there is first a slowing down of the cell metabolism between the initial temperature and 0° C., and then, between 0° and −20° C., the formation of ice crystals in the extracellular environment, thereby increasing the solute concentration of the culture medium. As a result, water begins to leave the cells and passes into the partially frozen extracellular medium, thereby initiating the cell dehydration and shrinking process. If the cooling process is rapid, intracellular ice crystals form before the end of the cell dehydration process. These ice crystals tear the cell membranes and organelles, causing death of the cell during the thawing process. If the refrigeration process is slow, the intracellular free water is expelled from the cell by osmotic force, leading to complete dehydration and shrinking of the cell. This can also cause cell death. However, when the cooling rate is sufficiently slow to prevent intracellular ice formation, but sufficiently rapid to avoid the serious effects of dehydration, the cells can survive the freezing and thawing processes. The survival zone or window is observable in many bacteria or other prokaryotes, but for most eukaryotic cells, it is nonexistent or very difficult to find without using cryoprotective agents. These agents have little effect on the damage caused by excessively fast freezing (formation of intracellular ice crystals), but generally prevent or decrease the damage due to slow freezing (dehydration and shrinking).

A large variety of chemical products are used to provide appropriate cryoprotection, including methylacetamide, methanol, ethylene glycol and polyvinylpyrrolidone. However, dimethyl sulfoxide (DMSO) and glycerol are the most practical and the most widely used. Several of these agents, although they provide excellent cryoprotection, have toxic side effects on the cultures, making them difficult to use. DMSO is most commonly used at a final concentration of 5% to 15% (v/v). Some cell lines are affected by more or less prolonged contact with DMSO. This effect can be reduced by adding the DMSO to the cell suspension at 4° C. during freezing, and by immediately removing it during thawing. Glycerol is generally used at a final concentration between 5% and 20% (v/v). Although it is less toxic to cells than DMSO, glycerol frequently causes osmotic problems, especially after thawing.

Thus, regardless of the cryoprotective agent used, it is necessary to rapidly dilute it or remove it during thawing of the cells. In certain cases, it is essential to remove the cryoprotective agent as completely as possible. This is the case, for example, when the thawed cells are very fragile or intended to be placed in coculture with fragile cells, as in the case of cocultures with embryos. This is also the case in cell therapy applications, when the thawed cells are intended to be injected into a patient: indeed, side effects have been observed after injection of hematopoietic cells in a solution containing DMSO (hypotension, heart rate disorder, convulsions, etc.). This removal is currently carried out by washing. Usually, after rapid thawing by placing the container in a water bath at 37° C., the cells are sterily transferred into a centrifugation tube, in order to perform one or more centrifugation steps with removal of the supernatant and resuspension in a culture medium not containing cryoprotective agent.

The multiplication of the pipetting, centrifugation, supernatant removal and resuspension steps leads to a risk of contamination of the thawed cells, and a technician and also equipment such as a centrifuge, a culture hood, etc., being unavailable for a relatively lengthy period of time. An objective of the present invention is to provide a simplified cell thawing method which makes it possible to very rapidly remove the cryoprotective agents while at the same time limiting the number of manipulations. This is obtained by using a filtering device such that the cells are retained on a filter through which the freezing medium passes. The present invention therefore relates to a cell thawing method comprising a step of thawing a cell suspension consisting of a freezing medium and of cells, followed by a step of removing said freezing medium by filtration. In the present text, a "cell suspension" denotes a solution of medium or buffer in which the cells, which may be adherent cells, are present in an essentially individualized manner, as opposed to a fragment of tissue, in which the cells are present in the form of an organized clump. Preferably, the step of removing the freezing medium is carried out without prior dilution of the cell suspension, as is frequently the case, for example in the methods described in the articles by Castino and Wickramashinge (*Journal of Membrane Science*, 1995), Xiaomin Zhou et al. (*Journal of Biochemical Engineering*, 2011), Perrotti et al. (*Transfusion*, 2004), Calmels et al. (*Bone Marrow Transplantation*, 2003) and Alghamdi et al. (*AJVR*, 2002). In a method according to the invention, the cryoprotective agents are preferably removed at the same time as the rest of the freezing medium, in a single and rapid step at the end of which the cells are temporarily separated from any medium, contrary to other methods described, in which the cryoprotective agents are gradually diluted by diffusion through a membrane, as described in U.S. Pat. No. 5,776,769 and also in the article by Arnaud et al. (*Platelets*, 2003). Thus, according to the invention, the step of removing the freezing medium is preferably carried out without prior or simultaneous provision of medium or a buffer.

According to one particular embodiment, the present invention relates to a cell thawing method comprising the following steps:
  (i) placing a first container, containing a frozen cell suspension, consisting of a freezing medium and of cells, at a temperature which allows the cell suspension to thaw;
  (ii) transferring the cell suspension from the first container into a device equipped with a filter, the pores of which have an average diameter of between 1 and 15 microns;
  (iii) placing said device in or above a second container, and applying to the cell suspension a force which drives the passing of the freezing medium through the filter;
  (iv) resuspending the cells retained on the filter, in a solution.

The "first container" of the above method, or "the container" of the methods described below in which a single container is necessary, may be any sterilizable hermetic container which withstands very low temperatures, such as a cryotube, a freezing bag, etc. Of course, this "first container" may consist of a set of containers, for example a set of 2 to 5 freezing tubes, the content of which will be combined in the filtration device. It is also possible to envision, as is described in the experimental section below, dividing the content of a freezing tube onto several centrifugal filters, in order to avoid clogging the filter. The freezing medium may be any medium conventionally used for storing cells, such as a mixture of culture medium (for example, DMEM), of serum (20%) or a serum substitute (such as KSR from Gibco) and of a cryoprotective agent such as DMSO.

According to another particular embodiment, the present invention relates to a cell thawing method comprising the following steps:
(i) placing a container, containing a frozen cell suspension, in a device equipped with a filter, at a temperature which allows the cell suspension to thaw;
(ii) applying to the cell suspension a force which drives the passing of the freezing medium through the filter;
(iii) resuspending the cells in a solution.

For carrying out the above method, it is necessary for the filter to have been chosen or treated so that, at the time of the introduction of the cell suspension to be frozen into the device equipped with a filter, the freezing medium does not pass through the filter. An example of filter treatment is described in example 5 below. It consists in adding to the filter, before the cell suspension to be frozen, a drop of a hydrophobic liquid. This liquid constitutes a temporary barrier between the filter and the cell suspension. During thawing, it is removed during the application of the driving force, which makes it pass through the filter. Any hydrophobic solution compatible with cell survival can be used to form this "temporary barrier" isolating the cell suspension from the filter. By way of example, mention may be made of glycerol and any sterile oil such as the endotoxin-free sterile oil used to cover embryos in order to prevent evaporation of the culture medium. Alternatively or additionally, a filter consisting of a hydrophobic material can be used, and also any other filter such that the freezing medium does not pass through before the application of a driving force which is necessarily greater than gravitational force g.

Conventionally, step (i) of the methods above will be carried out by placing the freezing tube(s) in a water bath at 37° C. or any other equivalent thermostatic device (such as a waterless bead bath, a heating block, etc.) for a period of a few seconds to a few minutes. The transfer performed in step (ii) of the first particular embodiment described above will preferably be carried out using a pipette, under sterile conditions, just like the resuspension of the cells retained on the filter, in the final step of the methods described above. Of course, these steps can be carried out manually by a technician, but they can also be partly or totally automated.

According to one particular implementation of the invention, the device equipped with a filter is a centrifugal filter.

According to another particular implementation of the invention, the average diameter of the pores of the filter is between 2 and 10 microns.

According to another particular implementation of the invention, the passing of the freezing medium through the filter is obtained by centrifuging the device equipped with a filter, placed in the second container. For example, this step can be carried out by centrifuging the device equipped with a filter for a period of less than or equal to 10 minutes (for example a simple "pulse", 10 seconds, 30 seconds, 1 minute, 3 minutes, 5 minutes or more), at a speed which makes it possible to apply to the cell suspension an acceleration of between 50 and 500 g, preferably between 100 and 200 g. Alternatively, this step can be carried out by applying an increased pressure on the side of the filter containing the cell suspension, and/or a reduced pressure on the other side of the filter.

According to one particular implementation of the method according to the invention, the amount of cells transferred in step (ii) or present right from step (i) in each filtration device is between $10^3$ and $5 \times 10^8$ cells, preferably between $10^4$ and $10^7$ cells per filtration device.

According to one particular implementation of the method according to the invention, the step of resuspending the cells is carried out by performing pipetting operations using a P200 or P1000 pipette. Several suction/discharge cycles can be carried out, so as to dissociate the cell clumps possibly formed.

The present invention also relates to a cell thawing kit comprising at least one tube of frozen cells and a device equipped with a filter, the pores of which have an average diameter of between 1 and 15 microns, preferably between 2 and 10 microns, said device being sterile.

According to one particular embodiment of the kit according to the invention, the cells have been frozen in the device equipped with a filter.

By way of nonlimiting examples of cells which can be included in such a kit, mention may be made of the following cells: VERO, L929, 3T3, Ishikawa, HeLa229, Jurkat, K562, COS-7, etc. The amount of cells present in the kit will of course depend on the intended application. The kit may, for example, contain 1, 2, 3, 4 or 5 tubes or more, each containing $2 \times 10^6$ VERO cells.

According to one particular embodiment of the kits of the invention, the device equipped with a filter is a centrifugal filter. In particular, the kit may contain 1, 2, 3 or 4 sterile centrifugal filters, packaged individually or in groups of 2 or more. These filters can have been sterilized by any appropriate means, for example by irradiation with gamma-rays.

The kits according to the present invention are particularly advantageous for implementing protocols requiring the use of feeder cells, as is the case for the culture of embryos, in particular in the context of in vitro fertilization (IVF). A ready-to-use kit for thawing and preparing feeder cells such as VERO cells in fact has the objective of facilitating the task of practitioners in their actions to promote the development of embryos up to the blastocyst stage and the implantation thereof, in the (therapeutic) human field, but also for veterinary applications, for selection and/or reproduction purposes, more particularly in cattle, members of the ovine family and members of the horse family.

According to one particular embodiment of the kits of the invention, the kit is intended to for promoting embryo culture; in addition to the frozen cells and the filtration device(s), such a kit may also comprise one or more of the following elements: 200 μl and/or 1000 μl sterile tips, a culture support for in vitro fertilization, sterile tubes and sterile pipettes. By way of example of a culture support suitable for IVF, mention may be made of Petri dishes and the BD Falcon™ or Nunc 4-well plate, for IVF, which are manufactured from crystalline virgin polystyrene tested according to USP Class VI standards. In the context of the present invention, a kit intended for promoting embryo culture may also comprise a rinsing medium and/or an embryonic culture medium and/or a culture medium for blastocysts and/or a sustained culture medium (for example CCM™).

The kits according to the present invention are also advantageously used for carrying out protocols for oocyte in vitro maturation (IVM), as is performed for overcoming infertility due to polycystic ovary syndrome (POS), or before chemotherapy.

According to one particular embodiment of the kits of the invention, the kit is intended for promoting oocyte in vitro maturation; in addition to the frozen cells and the filtration device(s), such a kit may also comprise one or more of the following elements: 200 μl and/or 1000 μl sterile tips, a culture support for oocyte in vitro maturation, sterile tubes and sterile pipettes. By way of example of a culture support suitable for IVM, mention may be made of Petri dishes and the BD Falcon™ or Nunc 4-well plate, for IVF, which are manufactured from crystalline virgin polystyrene tested according to USP Class VI standards. In the context of the present invention, a kit intended for promoting oocyte in vitro maturation may also comprise a rinsing medium and/or a culture medium for oocyte maturation (for example enriched with FSH and/or estradiol and/or gonadotropins).

According to another of its aspects, the present invention relates to a cell freezing kit, which comprises:

(i) a device equipped with a filter; and (ii) a container having hermetic closing means, capable of containing the device equipped with a filter (i), such that the filter is chosen in such a way that the freezing medium does not pass through in the absence of a driving force greater than gravitational force (for example, by virtue of hydrophobic properties), and/or such that the kit comprises a hydrophobic solution (water-immiscible) capable of passing through the filter only when a driving force greater than gravitational force is applied thereto. This hydrophobic solution, which may be, for example, a solution of glycerol or a sterile oil free of endotoxins, is intended to form a temporary barrier between the filter and the cell solution to be frozen, before the introduction of the cell suspension to be frozen into the device equipped with a filter.

In the cell freezing kits in accordance with the invention, the hermetic closing means of the container intended to receive the device equipped with a filter preferably comprise a screw cap. According to one preferred implementation, the container is similar to cell freezing tubes, suitable for containing a filter such as those which are in the Ultrafree® centrifugation filtration units (Millipore®), the "hermetic container+filter" assembly constituting, where appropriate, a centrifugation filtration unit. According to the formats and uses, the kits may contain one or more (2, 5, 10, 20 or more) sterile or sterilizable filtration units.

The following examples illustrate the invention without, however, limiting the scope thereof.

FIGURE LEGENDS

FIG. 1: Number of cells recovered after thawing and centrifugation in Ultrafree tubes.

Figure 2:
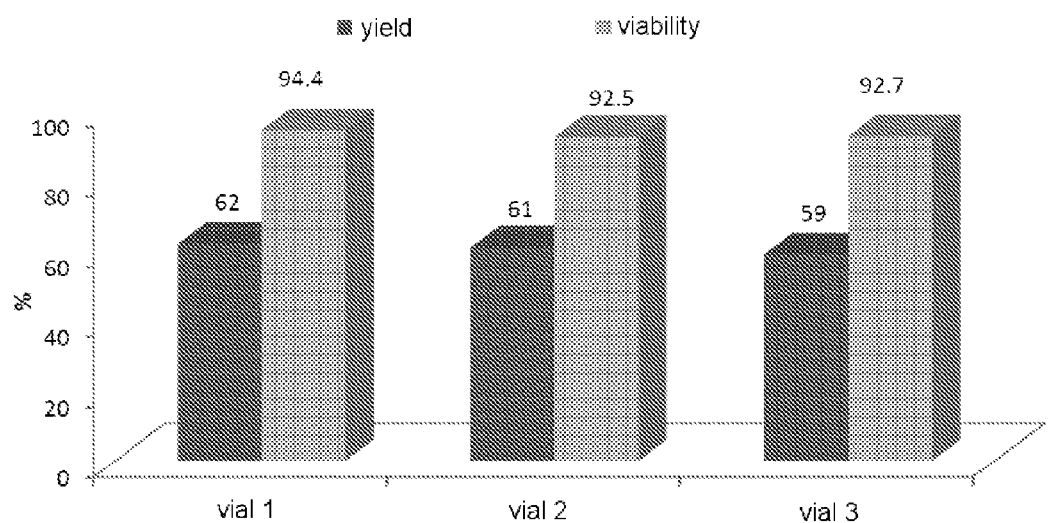

FIG. 2: Yield and cell viability of cells thawed and centrifuged in Ultrafree tubes.

Figure 3:
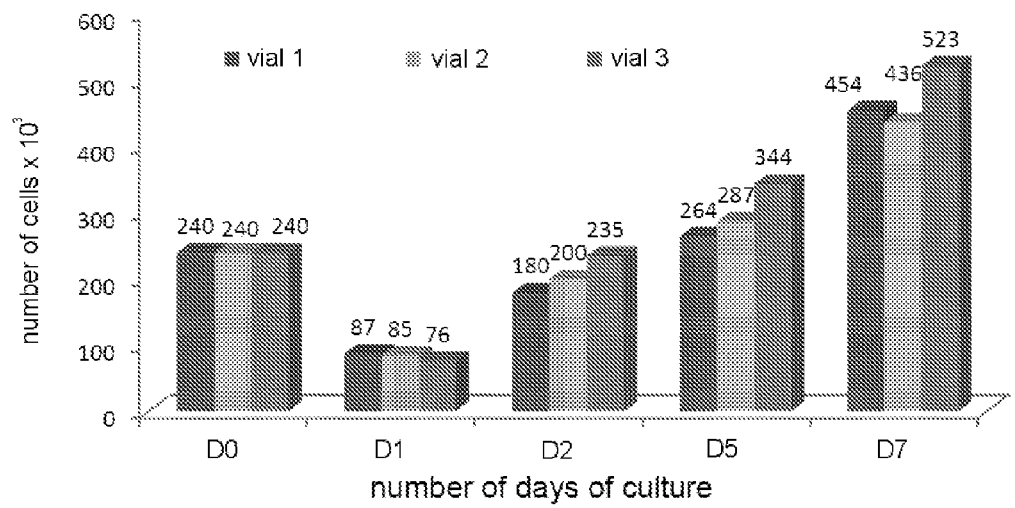

FIG. 3: Number of cells per well during the cell culture (cells thawed according to the Ultrafree tube technique and seeded in a 4-well plate).

Figure 4:
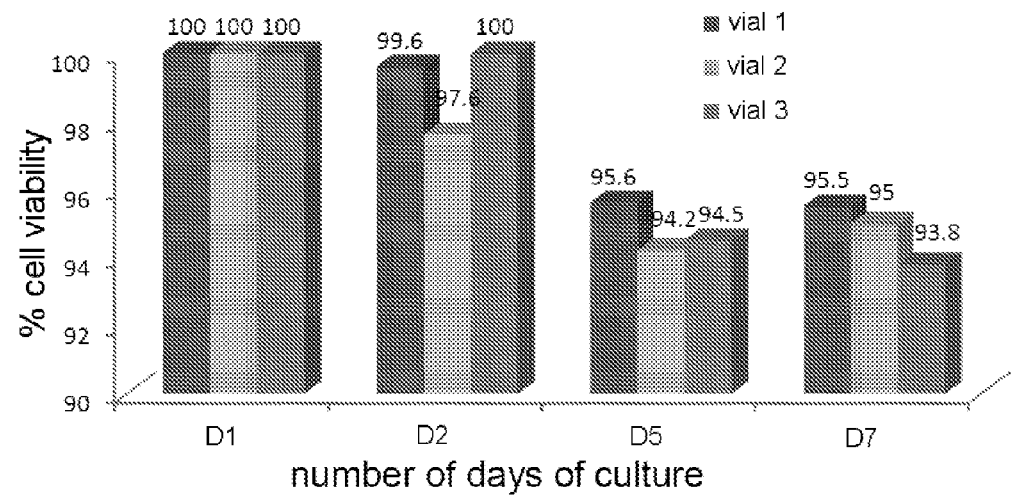

FIG. 4: Cell viability during culture (cells thawed according to the Ultrafree tube technique and seeded in a 4-well plate).

Figure 5:
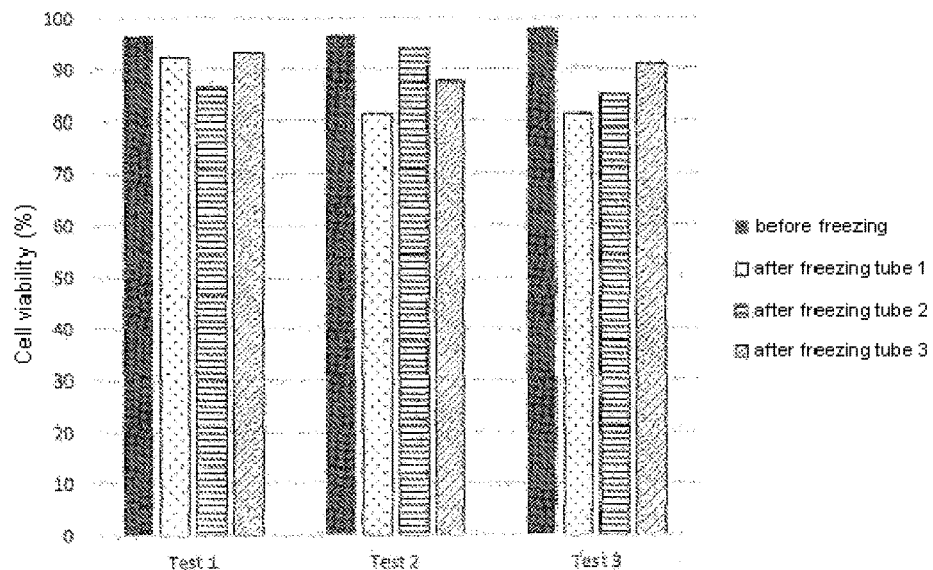

FIG. 5: VERO cell viability after 10 days of freezing at −80° C. in Ultrafree®-CL tubes, the membranes of which have been covered with 50 μl of glycerol.

Figure 6:
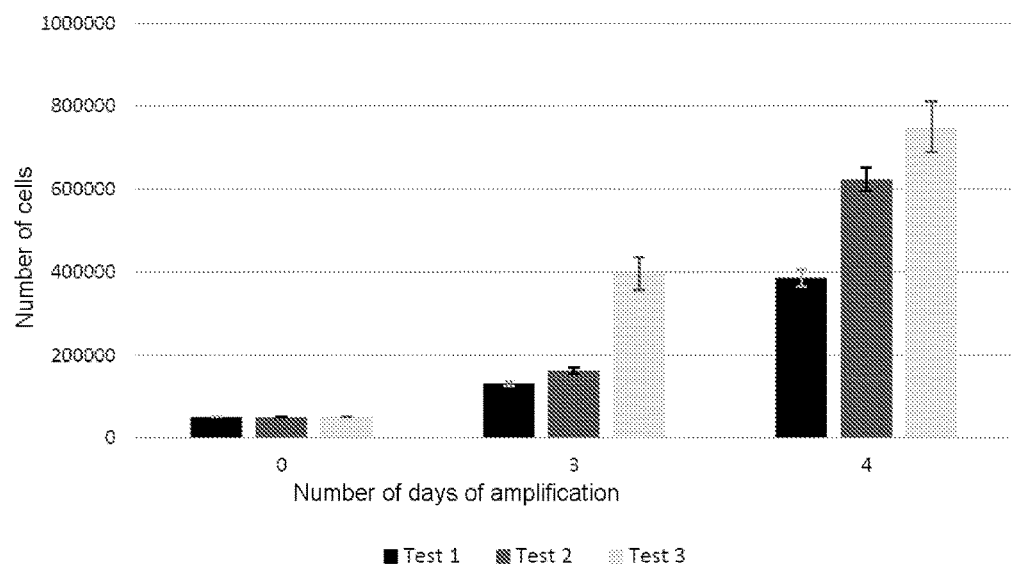

FIG. 6: Cell amplification after freezing in Ultrafree®-CL tubes.

EXAMPLES

Example 1: Use of the Thawing Columns (=Centrifugal Filters) for Thawing and Culturing Cryopreserved Cells Description of the Centrifugal Filters
   Ultrafree-CL SV centrifugal filters from Millipore:
   reference: UFC40SV25 Ultrafree-CL SV 5.0 centrifugal filters
   filter for microfiltration
   hydrophilic PVDF (polyvinylidene fluoride) filter
   filter pore size: 5.0 μm
   polypropylene device
   non-sterile.

Prior Process on the Centrifugal Filters
   In order to make them usable in cell culture, these centrifugal filters underwent the following treatment:
   welded individual polyethylene packaging (packaging can optionally be in several units)
   sterilization by irradiation with gamma-rays at 25 kGy (an amount of 8 kGy is sufficient).

The embryo toxicity of this device thus treated was tested by means of "Mouse embryo assays", demonstrating the innocuousness of the centrifugal filters on mouse embryo development up to the blastocyst stage.

Cells: monkey kidney cell line: Vero cells, cryopreserved in nitrogen vapor, at $2 \times 10^6$ cells/vial, with 1 ml of freezing medium: MEMa culture medium (80%)/fetal calf serum (10%)/dimethyl sulfoxide (10%).

Protocol:
Thawing of the Cryopreserved Cells
   Using one vial of cryopreserved VERO cells (Vero WHO, catalogue No. 88020401 at the ECACC)
   Place the vial in a water bath at 37° C. for 1 minute
   Homogenize the content of the vial
   Deposit 500 μl of cell suspension in each of the two sterilized UltraFree tubes
   Add 1 ml of MEMa medium to each of the centrifugal filters
   Centrifuge the Ultrafree centrifugal filters for 5 min at 100 g
   During the centrifugation:
      Prepare 1 15 ml tube (tube T1)
      Prepare 1 hemolytic tube containing 100 μl of trypan blue (tube T2).
   Recovery of the cells in the Ultrafree tubes at the end of centrifugation:
   Deposit 500 μl of CCM™-30 medium (Vitrolife, Göteborg, Sweden) on the filter of the first Ultrafree tube
   Carry out a series of 5 suction/discharge cycles on the whole of the filer
   Deposit the 500 μl of obtained suspension in the tube T1
   Deposit a further 500 μl of CCM medium on the filter of the same first Ultrafree tube
   Carry out a series of 5 suction/discharge cycles on the whole of the filter
   Deposit the 500 μl of obtained suspension in T1
   Carry out exactly the same manipulation on the second centrifugal filter.
   Homogenize the suspension of T1: "Suspension S1" (volume 2 ml)
   Sample and deposit 100 μl of the cell suspension S1 in T2 for counting
   Perform the cell count, and viability, by depositing the cell suspension between slide and cover slip of a hemocytometer Adjust the cell concentration to 480 000 cells/ml with CCM medium Seed 4 wells of an IVF plate at 240 000 cells/well (i.e. 500 µl/well).

Monitoring of the culture on D1

Observe the cultures

Trypsinize one well and perform a count/viability (+trypan blue)

Rinse the wells with 1 ml of PBS

Suction of the PBS

Add 300 µl of trypsin and place the cultures at 37° C. for 5 minutes

Suction and discharge (using a P200 and 200 µl tips) of the suspension until complete dissolution of the cell clumps Inhibit the action of the trypsin by adding 200 µl of medium for VERO cells Suction and discharge of the suspension until complete dissolution of the cell clumps Count the VERO cells using a hemocytometer.

Rinse the other wells with 1 ml of PBS/well.

Add 1 ml of CCM/well

Incubate the plates at 37° C.+5% $CO_2$.

Monitoring of the culture on D2=observation of the cultures and trypsinization of one well according to the description idem D1 (no change of medium).

Monitoring of the culture on D5=observation of the cultures and trypsinization of one well according to the description idem D1 (no change of medium).

Monitoring of the culture on D7=observation of the cultures and trypsinization of one well according to the description idem D1 (no change of medium).

Results

The experiment was carried out on three vials of VERO cells, and the results obtained are summarized in the graphs of FIGS. 1 and 2.

The results obtained show that the system for thawing VERO cells using the centrifugal filters makes it possible to recover more than one million live cells per vial of cells thawed. The cell viability is very satisfactory (greater than 90%), and the yield is also satisfactory (greater than 50%).

The results from placing back in culture the VERO cells thawed according to this Ultrafree centrifugal filter technique show a very good cell viability over time of greater than 90% over the course of 7 days of culture (FIGS. 3 and 4).

Moreover, the number of cells per well over time shows good cell growth starting from day 1. The drop in the number of cells between D0 and D1 after thawing and placing back in culture is observed in many cell types; it is explained by the fact that some cells may be viable at thawing without being capable of subsequently proliferating.

Starting from day D1, the number of cells per well gradually increases, and finally reaches close to 0.5 million per well on day 7 of culture, i.e. double the number of cells seeded.

The Vero cells thawed according to the Ultrafree tube technique are therefore viable and capable of proliferating in culture for 7 days. The results obtained on three tests show that this technique is reliable and reproducible.

Example 2: Use of the Thawing Columns (Centrifugal Filters) in a Ready-To-Use Kit for Thawing and Preparing VERO Cells for Mouse Embryo Development Up to the Blastocyst Stage Protocol:

On day D0: thaw one vial of VERO cells and seed 4 wells of an IVF plate, according to the protocol described in example No. 1.

On day D1: rinse each well with 1 ml of a buffer solution, and add 1 ml of CCM medium.

Deposit mouse embryos at the zygote stage: 10 embryos/well.

On day D2, evaluate the % of zygotes having reached the two-cell embryo stage.

On day 5: evaluate the % of 2-cell embryos having reached the blastocyst stage.

On day 6: evaluate the % of 2-cell embryos having reached the blastocyst stage.

Results

The experiment was carried out on three vials of VERO cells, and the results obtained are summarized below.

TABLE 1

|  | Day 2<br>2-cell embryo –/–<br>zygote | Day 5<br>Blastocyst –/– 2-cell<br>embryo |
|---|---|---|
| Vial 1 | 97% | 96% |
| Vial 2 | 97% | 96% |
| Vial 3 | 97% | 97% |
| Average | 97% | 96% |

The results obtained show that the system of thawing VERO cells using the centrifugal filters makes it possible to produce a cell layer suitable for the development of mouse embryos up to the blastocyst stage, and said embryos are also capable of growing. The blastulation rate on the cell layer of Vero cells is very satisfactory: more than 90%.

Example 3: Freezing/Thawing the Cells in One and the Same Container: Ultrafree Centrifugal Tube Freshly trypsinized Vero cells are frozen directly in the filter column of the Ultrafree tube (often incorrectly called "the filter"). The cells are then thawed in these same tubes.

Materials:

Description of the centrifugal filters: cf. example 1.

Prior process on the centrifugal filters: cf. example 1.

The glycerol used is the one from Euromedex, ref. 50405, purity>99.5%, molecular biology and electrophoresis grade. Cell culture glycerol can of course be used in place of the one used here, as can any liquid that is water-immiscible and compatible with cell survival/cell culture.

Cells: monkey kidney cell line: Vero cells, cryopreserved in nitrogen vapor, at $2 \times 10^6$ cells/vial, with 1 ml of freezing medium: MEMa culture medium (80%)/fetal calf serum (10%)/dimethyl sulfoxide (10%).

Culturing of cells: MEMα culture medium (95%)/fetal calf serum (5%).

Protocol:

Freezing of the Cell Suspension in the Ultrafree Tube Containing the Centrifugal Filter Starting from a suspension of freshly trypsinized cells in culture (viability measured=viability before freezing):

Prepare a suspension at 0.5 million/ml in freezing medium composed of 70% MEM-α (Gibco), 20% FCS, 10% DMSO;

Deposit 50 µl of glycerol on the centrifugal filter;

Deposit thereon 1 ml of the cell suspension in the freezing medium;

Prepare 3 centrifugal tubes in this way;

Close the Ultrafree tubes and place them at −80° C.

Thawing of the Cryopreserved Cells in the Same Ultrafree Tube Containing the Centrifugal Filter Place the 3 Ultrafree tubes containing the cell suspension in a water bath at 37° C. for 1 minute;

Centrifuge the tubes for 5 min at 100 g.

Recovery of the Cells on the Filter of the Ultrafree Tubes at the End of Centrifugation:

Deposit 500 µl of 95% MEM-α (Gibco), 5% FCS culture medium on the Ultrafree tube filter;

Carry out a series of 5 suction/discharge cycles on the whole of the filter:

Deposit a further 500 µl of culture medium on the Ultrafree tube filter;

Carry out a series of 5 suction/discharge cycles on the whole of the filter;

Place 1 ml final of the cell suspension in a 15 ml tube;

Sample and deposit 100 µl of the cell suspension for counting;

Perform the cell count, and viability, by depositing the cell suspension between slide and cover slip of a hemocytometer;

Seed in a 75 cm$^2$ flask and incubate the flasks at 37° C.+5% $CO_2$.

Result:

The entire test is reproduced three times, and the viability results are reported in FIG. 5. A viability of about 88.0% (±4.9) was obtained. FIG. 6 confirms that this technique is reliable and reproducible, the cells showing a good proliferation capacity after thawing.

The invention claimed is:

1. A cell thawing kit comprising at least one tube of frozen cells and one device equipped with a filter, the pores of which have an average diameter of between 1 and 15 microns, said device being sterile.

2. The kit as claimed in claim 1, wherein the cells have been frozen in the device equipped with a filter.

3. The kit as claimed in claim 1, wherein the cells are VERO cells.

4. The kit as claimed in claim 1, wherein the device equipped with a filter is a centrifugal filter.

5. The kit as claimed in claim 1, wherein the kit contains at least two sterile centrifugal filters.

6. The kit as claimed in claim 1, wherein the average diameter of the pores of the filter is between 2 and 10 microns.

7. The kit as claimed in claim 1, for promoting the embryo culture or oocyte in vitro maturation, wherein the kit also comprises one or more of the following elements: 200 µl and/or 1000 µl sterile tips, a culture support, sterile tubes, and sterile pipettes.

8. The kit as claimed in claim 1, for promoting the embryo culture or oocyte in vitro maturation, wherein the kit also comprises a rinsing medium and/or an appropriate culture medium.

9. The kit as claimed in claim 1, further comprising a container having hermetic closing means capable of containing the device equipped with a filter, wherein the filter has hydrophobic properties.

10. The kit as claimed in claim 9, wherein the hermetic closing means comprise a screw cap.

11. A cell thawing method using the cell thawing kit of claim 1, comprising a step of thawing a cell suspension consisting of a freezing medium and said frozen cells, followed by a step of removing said freezing medium by filtration using said device equipped with a filter, said step of removing the freezing medium being carried out without prior or simultaneous provision of medium.

12. The method as claimed in claim 11, comprising the following steps:
(i) placing a first container, containing a frozen cell suspension, at a temperature which allows the cell suspension to thaw;
(ii) transferring the cell suspension from the first container into the device equipped with a filter;
(iii) applying to the cell suspension a force which drives the passing of the freezing medium through the filter; and
(iv) resuspending the cells in a solution.

13. The method as claimed in claim 11, comprising the following steps:
(i) placing a first container, containing a frozen cell suspension in the device equipped with a filter, at a temperature which allows the cell suspension to thaw;
(ii) applying to the cell suspension a force which drives the passing of the freezing medium through the filter; and
(iii) resuspending the cells in a solution.

14. The method as claimed in claim 12, wherein the device equipped with a filter is a centrifugal filter.

15. The method as claimed in claim 12, wherein the average diameter of the pores of the filter is between 2 and 10 microns.

16. The method as claimed in claim 11, wherein the passing of the freezing medium through the filter is obtained by centrifuging the device equipped with a filter, placed in a second container.

17. The method as claimed in claim 16, wherein the device is centrifuged for a period of less than or equal to 10 minutes at a speed which makes it possible to apply to the cell suspension an acceleration of between 50 and 1500 g, preferably between 100 and 200 g.

18. The method as claimed in claim 12, wherein the passing of the freezing medium through the filter is obtained by applying an increased pressure on the side of the filter containing the cell suspension, and/or a reduced pressure on the other side of the filter.

19. The method as claimed in claim 12, wherein the amount of cells placed in each device equipped with a filter is between $10^4$ and $10^7$.

20. The method as claimed in claim 11, wherein the step of resuspending the cells is carried out by performing pipetting operations using a P200 or P 1000 pipette.

21. The method as claimed in claim 13, wherein the filter is hydrophobic, or, before the addition of the cell suspension to be frozen, has been covered with a hydrophobic liquid forming a temporary barrier between the filter and the cell suspension, said liquid being removed in step (ii) during the application of the driving force.

* * * * *